(12) United States Patent
Dan-Jumbo

(10) Patent No.: US 9,956,123 B2
(45) Date of Patent: May 1, 2018

(54) ANTI-MICROBIAL BALANCED WEAVE WEARABLE UNDERGARMENT AND PROCESS THEREFORE

(71) Applicant: Alpha1 Engineering Technology Group, Inc., Bothell, WA (US)

(72) Inventor: Eugene Dan-Jumbo, Bothell, WA (US)

(73) Assignee: Alpha1 Engineering Technology Group, Inc., Bothell, WA (US)

( * ) Notice: Subject to any disclaimer, the term of this patent is extended or adjusted under 35 U.S.C. 154(b) by 245 days.

(21) Appl. No.: 15/058,925

(22) Filed: Mar. 2, 2016

(65) Prior Publication Data

US 2017/0252224 A1 Sep. 7, 2017

(51) Int. Cl.

| A61F 13/15 | (2006.01) |
|---|---|
| A61F 13/42 | (2006.01) |
| A61F 13/49 | (2006.01) |
| A61F 13/495 | (2006.01) |
| A61F 13/496 | (2006.01) |
| A61F 13/511 | (2006.01) |
| A61F 13/58 | (2006.01) |
| A61F 13/84 | (2006.01) |

(52) U.S. Cl.
CPC ............ *A61F 13/42* (2013.01); *A61F 13/495* (2013.01); *A61F 13/496* (2013.01); *A61F 13/49007* (2013.01); *A61F 13/51121* (2013.01); *A61F 13/58* (2013.01); *A61F 13/8405* (2013.01); *A61F 2013/422* (2013.01); *A61F 2013/51139* (2013.01); *A61F 2013/586* (2013.01)

(58) Field of Classification Search
CPC .. A61F 13/42; A61F 13/49007; A61F 13/495; A61F 13/496; A61F 13/51121; A61F 13/58; A61F 13/8405; A61F 2013/422; A61F 2013/51139; A61F 2013/586
USPC ......... 604/361, 367, 385.101, 384, 378, 396
See application file for complete search history.

(56) References Cited

U.S. PATENT DOCUMENTS

| 3,109,428 A | 11/1963 | Jamison |
| 4,985,025 A | 1/1991 | Lingertat et al. |
| 5,843,542 A | 12/1998 | Brushafer et al. |
| 6,124,221 A | 9/2000 | Gabbay |
| 6,381,482 B1 | 4/2002 | Jayaraman et al. |

(Continued)

OTHER PUBLICATIONS

PCT International Search Report, dated Jun. 15, 2017, regarding Application No. PCT/US2017/018232, 4 pages.

*Primary Examiner* — Jacqueline Stephens
(74) *Attorney, Agent, or Firm* — Yee & Associates, P.C.

(57) ABSTRACT

In an embodiment, a garment, such as a smart pull-up, includes at least one outer section and a midsection attached to the outer section. The midsection includes a first antimicrobial membrane patch layer configured to contact a wearer's body, a second antimicrobial membrane patch layer disposed adjacent to the first antimicrobial patch layer, and an air gap disposed between the first patch and second antimicrobial patch layers. The first and second antimicrobial patch layers each are formed from respective balanced warp big tows and fill tows in a plain-weave pattern, and each layer include copper filaments disposed in a plurality of the tows, each of the copper filaments including at least $Cu^+/Cu^{+++}$ ions. Such a smart pull-up may be suitable for either adult who cannot use the toilet, or child, or healthy adult and, therefore, may urinate and defecate himself/herself.

28 Claims, 9 Drawing Sheets

(56) References Cited

U.S. PATENT DOCUMENTS

| | | |
|---|---|---|
| 8,975,465 B2 | 3/2015 | Hong et al. |
| 2004/0167483 A1 | 8/2004 | Gabbay |
| 2005/0112085 A1 | 5/2005 | MacDonald et al. |
| 2012/0202684 A1 | 8/2012 | MacDonald |
| 2013/0012907 A1 | 1/2013 | Sasayama et al. |
| 2014/0096420 A1 | 4/2014 | Ronner et al. |
| 2016/0038628 A1 | 2/2016 | Klofta et al. |

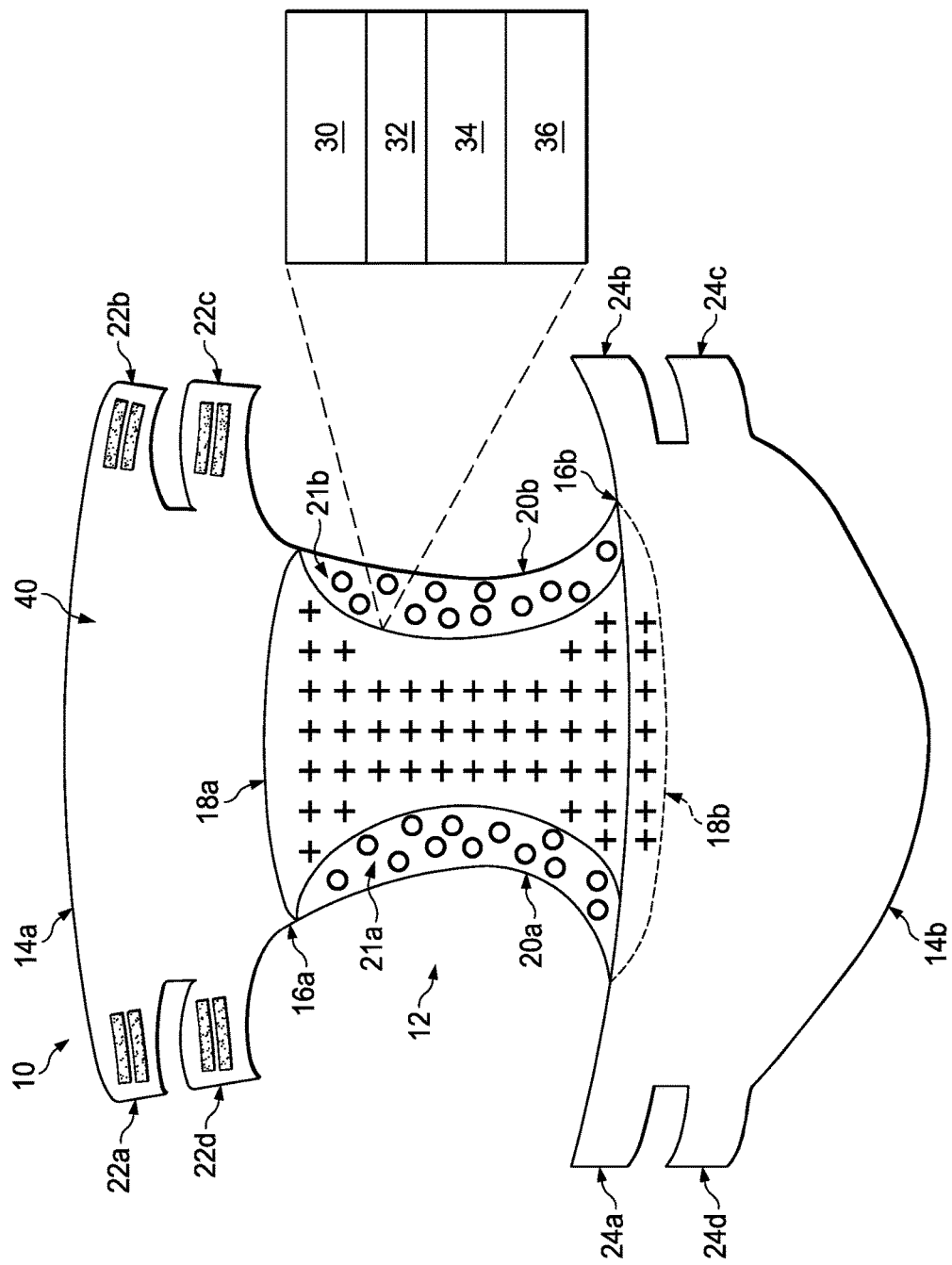

ANTI-MICROBIAL BALANCED WEAVE WEARABLE UNDERGARMENT AND PROCESS THEREFORE

BACKGROUND

As individuals age or develop certain medical conditions, incontinence may result. Thus, some individuals may choose to wear an undergarment specifically designed to hold urine or feces when incontinence is an issue. Of course, the smart undergarment may be well designed to prevent any urine or feces from escaping from a chamber within the smart undergarment, however, the urine or feces will remain in contact with the skin of the wearer until the undergarment can be changed. In some situations this may be a matter of hours or even up to a day. Thus, the skin of the wearer may develop maladies, such as rash or sores or others as a result of the urine of feces remaining in contact with the skin for greater lengths of time.

Urine and feces often contain bacterium or viruses that can interact and multiply when in contact with the skin. Further, sub-layers of skin may also become infected with these bacterium or viruses and when interacting with additional substances, such as air and moisture, multiplication leads to stronger odor, more skin irritation, rashes, and sores. Stopping, preventing, or otherwise killing these bacterium and viruses are a goal of any smart undergarment suited for this purpose.

For healthy adults with occasional bladder leaks, or prostate leaks or other medical biological leaks; this novel fail-safe smart undergarment anti-microbial design may be useful to hold or even prevent the outward egression of either urine or other bodily excretion.

SUMMARY

In an embodiment, a garment, such as an adult pull-up, includes at least one outer section and a midsection attached to the outer section. The midsection includes a first antimicrobial layer configured to contact a wearer's body, a second antimicrobial layer disposed adjacent to the first antimicrobial layer, and an air gap disposed between the first and second antimicrobial layers. The first and second antimicrobial layers each are formed from respective balanced warp tows and fill tows in a plain-weave pattern, and each layer include copper micro filaments or fibers disposed in a plurality of the tows, each of the copper micro filaments or fibers including at least $Cu^+$ ions. Such a smart pull-up undergarment may be suitable for a healthy adult, or children or an adult who cannot use the toilet, and, therefore, may urinate and defecate himself/herself.

In an embodiment, the unique design of the pull-up wicks away a significant amount of excrement and other excretions (e.g., sweat) from the pull-up wearer's skin while resisting tearing that may otherwise occur in response to the stresses and strain caused by defecation and movement of the wearer, and the antimicrobial properties of the pull-up fight infection, rash, bed sores, and other skin irritations that may otherwise occur in response to any un-wicked excrement contacting the pull-up wearer's skin. The midsection of the pull-up, which is configured for covering the genital and anal areas of the wearer, includes first and second antimicrobial membrane layers with an air gap in between the layers. When the wearer urinates or defecates, at least some of the excrement passes through the first membrane layer closest to the wearer's skin into the gap, which effectively holds the excrement away from the wearer's skin. The first layer includes micro copper strands or filaments with $Cu^+$, $Cu^{++}$, $Cu^{+++}$ ions that penetrate the wearer's skin to prevent infection, rash, bed sores, and other maladies that may be caused by excrement contacting the wearer's skin for an extended period of time, e.g., between the bio-under garment changes. The second membrane layer also includes micro copper filaments with $Cu^+$, $Cu^{++}$, $Cu^{+++}$ to sterilize the excrement in the air gap. Furthermore, the big tow weave pattern of the midsection provides tensile strength & durability to the smart pull-up design even under the stresses and strains caused by defecation and movement of the wearer.

In yet another embodiment, the pull-up includes one or more embedded multi-functional nano-copper sensors that can sense excrement, can indicate the presence of excrement, and can indicate when excrement has been present for more than a threshold period of time. For example, the sensor can indicate the presence of excrement by changing color, and can indicate when excrement has been present for more than a threshold period of time by changing to another color.

BRIEF DESCRIPTION OF THE DRAWINGS

FIG. 1 is an isometric unfolded view of a pull-up in an open configuration ready to engage a person, according to an embodiment.

DETAILED DESCRIPTION

Figure 3:
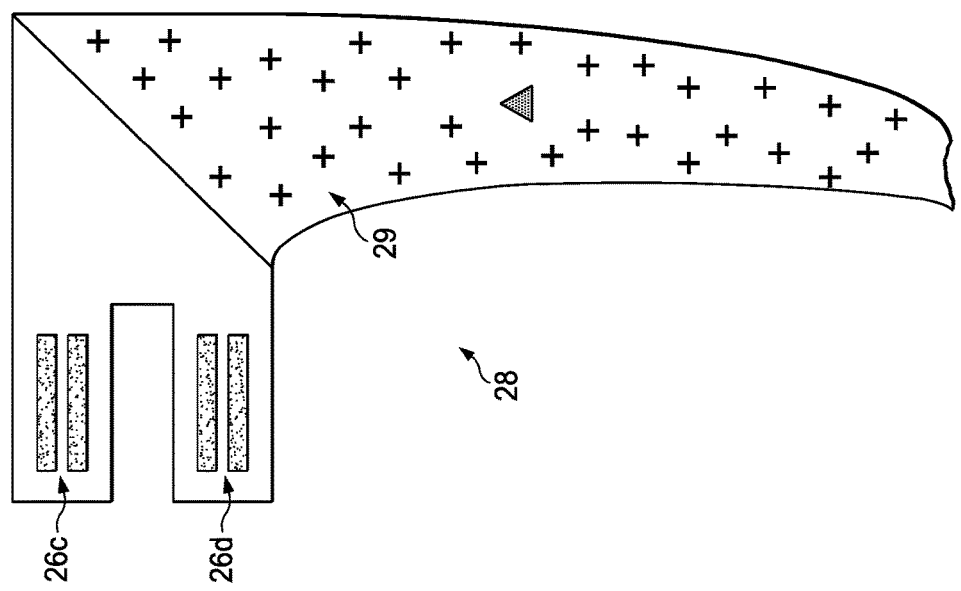
FIG. 3 is a plan view of a right-side flaperon leg extension configured to be attached to the pull-up of FIG. 1, according to an embodiment.

The use of transitional metals, such as copper (Cu) and its alloys, as antimicrobial (e.g., antibacterial, antifungal, and antiviral) agents is known, and the literature describes such metals as being used in clothing to prevent odor (by killing odor-causing bacteria), to prevent rashes (e.g., in a garment), etc. For example, U.S. Pat. No. 6,124,221, and U.S. Patent Publication 2004/0167483, both to Gabbay, disclose garments that have $Cu^{++}$ copper (copper with $Cu^{++}$ ions) plated onto the garment material. But Gabbay's garment has significant problems. For example, it is theorized that $Cu^{++}$ ions are more toxic in plated form than other Cu ions such as $Cu^+$ and $Cu^{++}$, and $Cu^{+++}$ combined at either the atomic or ionic state.

Furthermore, substances, other than $Cu^{++}$, (e.g., palladium, zinc) generated during Gabbay's plating process may remain on Gabbay's heavy garment material after the plating process is completed, and may constitute 3%-10% of the combined weight of the plated substances. Unfortunately, these other substances may be toxic, even carcinogenic, to humans. For example, such other substances may cause tissue damage to the skin, and neural degradation of nerves in or near the skin. Moreover, these other substances may diminish the efficacy of Gabbay's $Cu^{++}$ ions in killing bacteria, viruses, and other microbes and microorganisms.

In addition, Gabbay's garment cannot indicate the presence of excrement so that a caregiver can more easily determine when it is time to remove the soiled garment, clean the garment wearer, and replace the soiled garment with a clean garment. Therefore, a wearer of Gabbay's garment may be in a soiled garment for a relatively long period of time, particularly when the caregiver is busy with other patients and does not have time to physically check the wearer's garment for signs of soiling. Described below are embodiments of an adult or child pull-up that does not suffer from one or more of these problems, and that may have additional advantages, with novel design.

In an embodiment, an adult pull-up includes micro copper filaments with $Cu^+$, $Cu^{++}$, $Cu^{+++}$ ions. The use of filaments instead of plating eliminates, from the pull-up, other substances that are possibly toxic and that may reduce the antimicrobial efficacy of the $Cu^+$ ions. And it is theorized that combined $Cu^+$, $Cu^{++}$, $Cu^{+++}$ ions are more effective, adaptive, and less toxic than $Cu^{++}$ ions alone in killing and preventing microbes in and on human skin. More specifically, it is theorized that $Cu^+$, $Cu^{++}$, $Cu^{+++}$ ions enter the cell membrane DNA of a bacterium/virus, and change the electrical potential of the cell membrane by binding with an enzyme in the bacterium/virus membrane. This local biochemical hyper polarized network results in creating an inhibitory protein molecular structure that damages or degrades the microbe's cell membrane anatomy—and reduces the biological energy-producing ability of the microbe cell, thus "suffocating" the cell so that cell cannot multiply in or on human skin anatomy. The micro copper filaments may also include $Cu^{+++}$ ions, which are also theorized to be more effective, adaptive, and less toxic than $Cu^{++}$ ions in killing (99%), reducing, and preventing microbes in and on human skin. By killing, reducing and preventing microbes in and on human skin, the $Cu^+$ and $Cu^{+++}$ ions can prevent, and mitigate the intensity of, skin irritations such as skin infections, rashes, sores, and other maladies of the skin, that may lead to more complex medical attention.

In another embodiment, the adult pull-up also includes one or more nano-copper sensors that are configured to sense excrement (e.g., feces, urine) and to generate a notification that excrement is present in the pull-up. For example, such a nano-copper sensor may be configured to sense the stresses and strains (i.e., an abuse load) imparted to the pull-up by solid feces, and to change color in response to sensing this load or strain. Furthermore, such a nano-copper sensor may also be configured to sense a liquid, such as urine or liquid present in loose feces, and to change color in response to sensing the liquid. The color that the sensor changes to in response to sensing a load or strain may be the same, or may be different, than the color that the sensor changes into in response to sensing a liquid. And if the sensor senses both a load and a liquid, it may change into yet a different color than the colors for sensing only load or only a liquid. Moreover, after sensing a load, liquid, or both a load and liquid, for a threshold period of time, the sensor may change into yet another color to indicate that excrement has been present in the pull-up for at least the threshold period of time. Such an indication can inform a caregiver that the wearer urgently needs a pull-up change.

FIG. 1 is an isometric view of a garment, here an adult pull-up, 10 in a flattened configuration, according to an embodiment. As described above and below, the adult pull-up 10 has antimicrobial properties, and may also have one or more sensors to detect and indicate the presence of excrement, and to detect and indicate the amount of time for which the excrement has been present.

The adult pull-up 10 includes a midsection 12, which is configured to cover the anal and genital regions of a wearer (not shown in FIG. 1), and two outer sections 14a and 14b, which are secured to opposite ends 16a and 16b of the midsection along respective seams 18a and 18b.

The midsection 12, which is further described below, is configured to cover the anal and genital regions of a wearer's body (not shown in FIG. 1) and has tapered edges 20a and 20b to comfortably fit around the legs of the wearer. The pull-up includes micro copper filaments (described more below) that release complex copper ions to kill or reduce microbes such as bacteria and viruses, and may include one or more nano-copper sensors to sense and indicate the presence and duration of excrement. The edges 20a and 20b may each include a respective elastic band 21a and 21b, or another elastic material, to provide a snug fit around the legs of the wearer.

The outer section 14a, which is further described below, includes adhesive, double-split flaperons 22a-22d, and the outer section 14b includes non-adhesive, double-split flaperons 24a-24d.

The flaperons 22 and 24, which are described in more detail below, allow one to configure the pull-up 10 into a wearable form that comfortably fits around the legs, gluteus, genitals, and lower abdomen of the wearer. That is, the flaperons 22 and 24 allow one to conform the pull-up to the body contours of the wearer, and to adjust, and, if necessary, to readjust, the configuration of the pull-up, for a "custom fit." In one embodiment, the flaperons may secured to a counterpart flaperon, such as 22a to 24a, 22d to 24d, etc. In other embodiments, the flaperons 22 and 24 adhere to the wearer skin without reaching full around to come into contact with a counterpart flaperon.

Once the flaperons 22 are secured to the respective flaperons 24 to form the bio-engineered antimicrobial smart pull-up, the wearer, or the wearer's caregiver, can take the pull-up off of the wearer, and can put the pull-up back onto the wearer, like a pair of shorts or underwear. The bio-engineered antimicrobial smart pull-up's rugged construction (described further below) allows the pull-up to be taken off and re-worn multiple times, at least as long as the wearer does not excrete excrement or other excretions into the pull-up. The bio-engineered antimicrobial smart pull-up could also be disposed of when configured in a less superior material form (e.g., paper or other materials)

In FIG. 1, there is also shown a cutaway side view of the midsection 12 of the pull-up 10 such that various layers or membranes of the midsection 12 can be shown. Although a skilled artisan understands that the layers can be membranes, the term layer is used throughout this disclosure for simplicity sake. The midsection includes a first layer 30, an air gap 32, a second layer 34 disposed on the other side of the air gap from the first layer, and an optional third layer 36.

The first layer 30, which is further described below, is the layer that is closest to, and contacts, the wearer's skin, and is formed from a biodegradable, anti-allergenic, super-absorbent, fluid semi-permeable material that is rugged enough to enable the pull-up 10 to be worn multiple times, and to resist ripping and tearing upon exposure to the liquids present in urine and feces, and upon bearing a load caused by solid feces.

The first layer 30 also includes micro copper filaments (not shown in FIG. 2) that, when wetted by urine or liquid in feces, release copper ions, including at least $Cu^+$ and $Cu^{+++}$ ions, to kill or reduce or prevent bacteria, viruses, and other microbes. As discussed above, these copper ions diffusion into the human skin not only kill or reduce or prevent microbes within the first layer 30 itself, but penetrate the wearer's skin and kill or reduce or prevent microbe penetration in or on the skin. By killing or reducing or preventing microbes in the first layer 30, the copper ions reduce or eliminate the odor often caused by urine and feces, and by killing or reducing microbes in and on the wearer's skin, the copper ions prevent, or mitigate the intensity of, infection, rash, bed sores, and other skin irritations that may result from excrement contacting the skin.

And the first layer 30 may also include one or more nano-copper sensors that are configured to sense the presence of excrement contacting the first layer, and to indicate the presence of excrement by, e.g., changing color. As described below, the nano-copper sensors may actually be embedded in the first layer 30, or may be attached to the first layer. Furthermore, as also described below, the micro copper filaments that provide the antimicrobial copper ions may form part of at least one of the nano-copper sensors.

The air gap 32 acts as a repository, or reservoir, for urine, feces, and other excretions (e.g., sweat) that pass through the first layer 30; that is, the air gap holds excrement away from the wearer's skin to help prevent, or to mitigate the intensity of, infection, rash, bed sores, and other skin irritations. Another way to describe the operation of the first layer 30 and the air gap 32 is to say that the air gap allows the first layer to wick away, from the wearer's skin, urine, liquid from feces, and other liquids (e.g., sweat), and to deposit these liquids into the air gap. Furthermore, copper ions released from the micro copper filaments in the first layer 30 may also migrate into the gap 32, and, therefore, may effectively sterilize the excrement in the gap by killing microbes therein. Moreover, the air gap 32 may also serve as a percolating gap that starves bacteria of the oxygen that the bacteria need to multiply, and this starvation, which is in addition to the antimicrobial action of the copper ions, may aid in preventing odor, and preventing/mitigation infection/irritation of the wearer's skin. In addition, the air gap 32 may include one or more nano-copper sensors configured to sense excrement, to indicate the presence of excrement, and to indicate the persistence of the excrement.

Still referring to FIG. 1, the second layer 34 is similar in structure and operation to the first layer 30, and acts as a failsafe design layer to kill or reduce any microbes that are present in excrement that passes from the air gap 32 into the second layer. Furthermore, because the second layer 34 is closer to the outside of the pull-up 10 than is the first layer 30 and the air gap 32 (at least when the pull-up is being worn), the excrement indication provided by the one or more nano-copper sensors in the second layer may be better noticed by a caregiver or wearer than the excrement indication provided by the one or more nano-copper sensors in the first layer or in the air gap.

The optional third layer 36 is made from a liquid-impermeable material, such as cotton padding or paper, to prevent liquid excrement from leaking out from the pull-up 10. The third layer 36 may be attached to the second layer 34 according to any suitable technique such as with stitching or with an adhesive. The outer section 14a includes a fourth layer 40, which is formed from a biodegradable, anti-allergenic, super-absorbent, fluid-impermeable material that is rugged enough to enable the pull-up 10 to be worn multiple times or disposed of, and to resist ripping and tearing upon exposure to the liquids present in urine and feces, and upon bearing a load caused by solid feces. Although it is contemplated that the midsection 12 will contain the bulk of the urine and feces excreted by the wearer of the pull-up 10 (FIG. 1), it is contemplated that urine and feces may also migrate to the outer section 14a (i.e., to between the wearer's skin and the fourth layer 40).

Therefore, the fourth layer 40 may include micro copper filaments (not shown in FIG. 1) that, when wetted by urine or liquid in feces, release copper ions, including at least $Cu^+$ and $Cu^{+++}$ ions, to kill bacteria, viruses, and other microbes as described above in conjunction with the first layer 30 of the midsection 12. Further, the fourth layer 40 may include one or more nano-copper sensors that are configured to sense the presence of excrement contacting the first layer, to indicate the presence of excrement by, e.g., changing color, and to indicate the persistence of the excrement by changing color again, as described above in conjunction with the first layer 30 of the midsection 12.

The fourth layer 40 extends between the ends of the first and second layers 30 and 34, and is secured to the first and second layers by the seam 18a, which may be formed by any conventional technique such as stitching, gluing, or matting. And the third layer 36 extends from the midsection 12 over the fourth layer 40 to prevent liquid excrement from leaking out from the pull-up 10. The third layer 36 may be attached to the fourth layer 40 in any suitable manner, such as with an adhesive. Furthermore, although the seam 18a is described as going through the third layer 36, the seam 18a may not go through the third layer.

Further, the first layer 30 may include two outer sublayer and a center sublayer. The outer sublayers may be attached to the sublayer in any suitable manner such as by gluing. Alternatively, the two outer sublayers may be formed over the sublayer as a coating. The two outer sublayers are formed from a micro foam, such as a cellulose honeycomb core foam, that is natural, super absorbent, biodegradable, and non-allergenic. This foam absorbs and holds urine, liquid from feces, and other liquids (e.g., sweat). When the foam becomes saturated, the excess liquid passes into the gap 32 as described above. In this way, the two outer sublayer act to wick moisture away from the wearer's skin and into the gap 32. The center sublayer, embodiments of which are described below, includes the copper filaments (not shown in FIG. 1) that provide the copper ions for killing or reducing microbes, provides tensile strength and ruggedness to the first layer 30, and may include one or more nano-copper sensors for sensing, and indicating the presence of, excrement. Alternate embodiments of the first layer 30 are contemplated. For example, one, or both, of the outer sublayers may be omitted. Furthermore, the center sublayer may include foam material that is similar to the foam that forms the sublayers.

Alternate embodiments of the pull-up 10 are contemplated. For example, the pull-up 10 may include a single flaperon per side of the outer sections 14a and 14b, or may include more than two flaperons per side or no flaperon but a seam (FIG. 11). Furthermore, although described as an adult pull-up, the pull-up 10 may be sized for a child.

Figure 2:
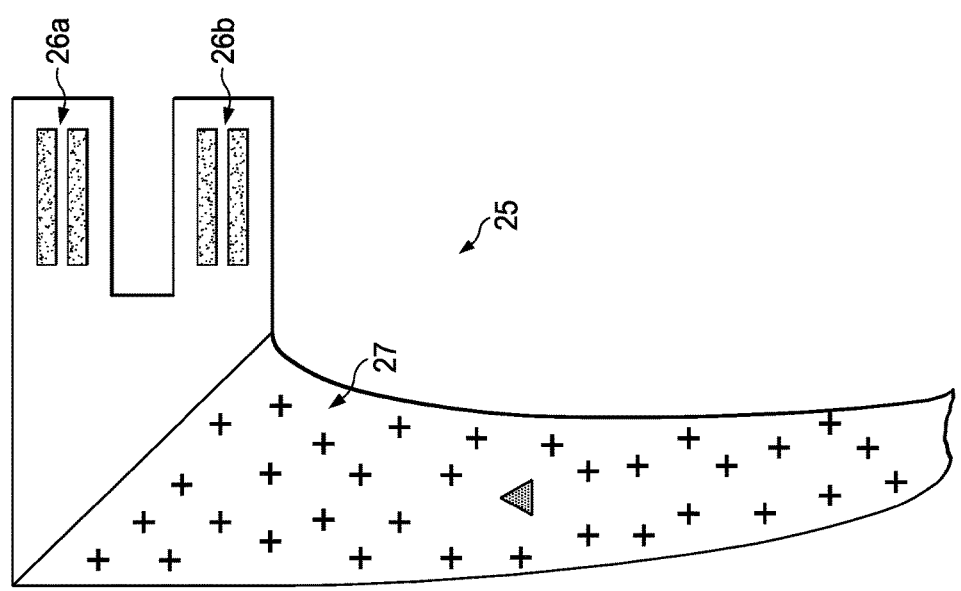
FIG. 2 is a plan view of a left-side flaperon leg extension configured to be attached to the pull-up of FIG. 1, according to an embodiment.

FIG. 2 is plan view of a left-side leg extension 25 configured to be attached to the pull-up of FIG. 1, according to an embodiment. In this plan view, a left-side leg extension is shown such that this extension 25 may adhere to a leg area of a wearer. In other embodiments, the leg-extension 25 may adhere to the pull-up 10 of FIG. 1. Similar to the flaperons of FIG. 1, the left-side leg-extension includes flaperons 26a and 26b that may include one or more adhesive strips. Further, the leg-extension may include an absorbent area 27 that has similar characteristics to the midsection 12 of FIG. 1. That is, absorbent area 27 includes embedded woven anti-microbial $Cu^+$, $Cu^{+++}$ ions integrated within a balanced plain big tow weave fabric or superior paper. The left-side body-leg extension 25 includes angles suited to pick up excretion waste in solid and liquid forms that may escape the pull-up 10.

FIG. 3 is plan view of a right-side leg extension configured to be attached to the pull-up of FIG. 1, according to an embodiment. In this plan view, a right-side right extension is shown such that this extension 28 may adhere to a leg area of a wearer. In other embodiments, the leg-extension 28 may adhere to the pull-up 10 of FIG. 1. Similar to the flaperons of FIG. 1, the right-side leg-extension includes flaperons 26c and 26d that may include one or more adhesive strips. Further, the leg-extension may include an absorbent area 29 that has similar characteristics to the midsection 12 of FIG. 1. That is, absorbent area 29 includes embedded woven anti-microbial $Cu^+$, $Cu^{+++}$ ions integrated within a balanced plain big tow weave fabric. The left-side body-leg extension 28 includes angles suited to pick up excretion waste in solid and liquid forms that may escape the pull-up 10.

Figure 4:
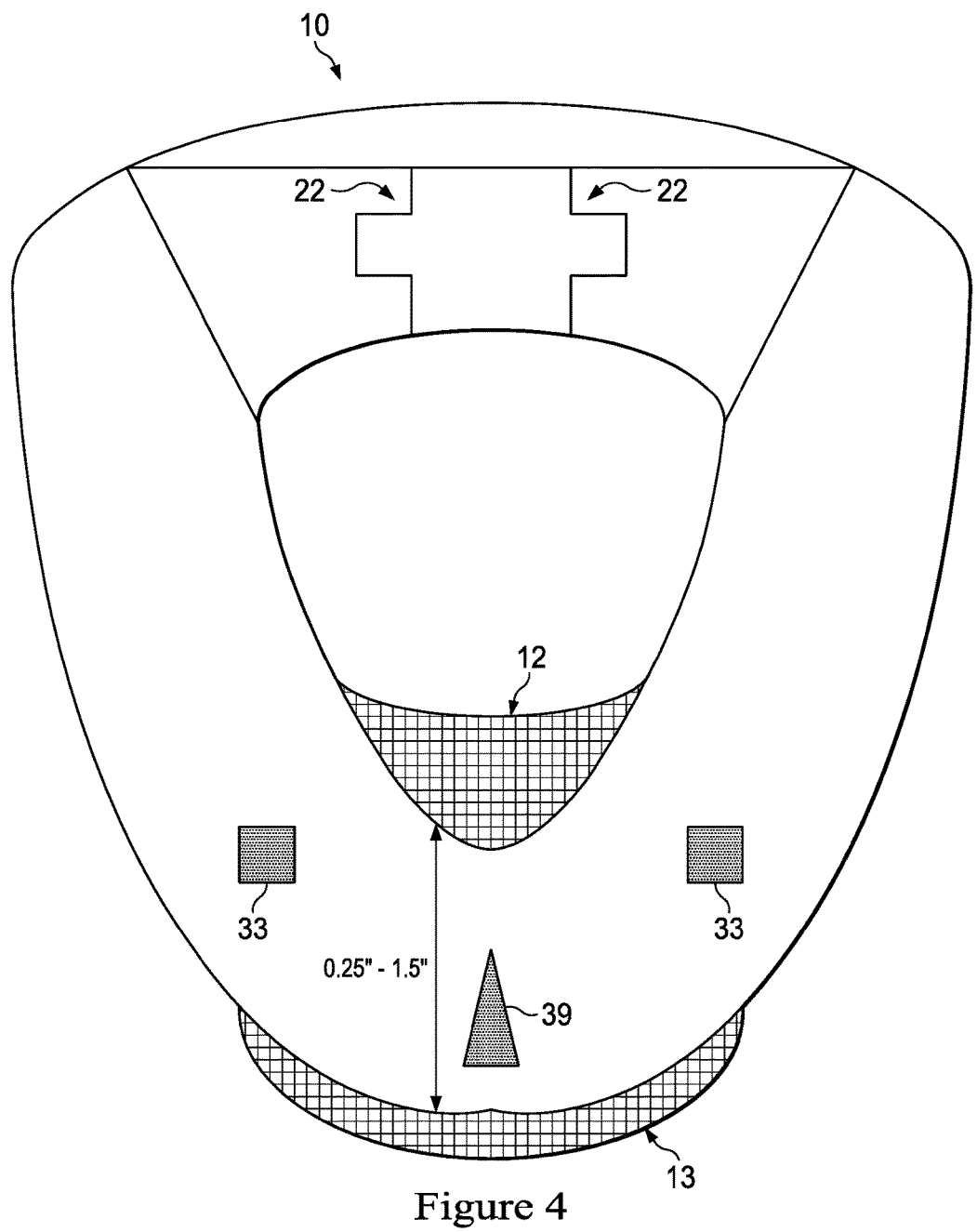
FIG. 4 is a side view of the pull-up of FIG. 1 shown in an engaged form according to an embodiment.

FIG. 4 is a side view of the pull-up of FIG. 1 shown in an engaged form according to an embodiment. The pull-up 10 is shown having the front flaperons 22 attached to an attachment area such as another garment, a human abdomen or the like. In this embodiment, the midsection 12 is shown on an inner membrane patch portion of the pull-up 10 such that the inner midsection 12 contacts the skin of the wearer. Further, this embodiment also shows an outer midsection 13 that is similar to the inner midsection 12. That is, both the inner midsection 12 (sometimes called primary antimicrobial layer) and the outer midsection 13 (sometimes called secondary microbial patch layer) include embedded anti-microbial Cu+, Cu+++ microfilaments to kill/reduce bacterial and viral infections. The outer midsection 13 provides additional contact with the inner thighs of the wearer and assists with handling excretion that may escape the pull-up 10. Further yet, the distance between the inner midsection 12 and the outer midsection 13 may be typically 0.25 inches to 1.5 inches thereby providing a percolating gap 39 reserve membrane to isolate bacteria from oxygen so as to disrupt or delay the biochemical process.

The embodiment of FIG. 4 shows two load and liquid micro-nano-copper-sensors 33. These micro nano-sensors are self-regulated to detect the presence of liquid excretion or solid excretion. In various embodiments, more than two may be used and various micro-nano-copper-sensors 33 may be configured to detect only liquid excretion or only solid excretion. Further, the nano-sensors 33 may track elapsed time since first detection such that the data and information about parameters being sensed may be transferred to a local mobile device, if so desired within a medical settings or wearer.

Figure 5:
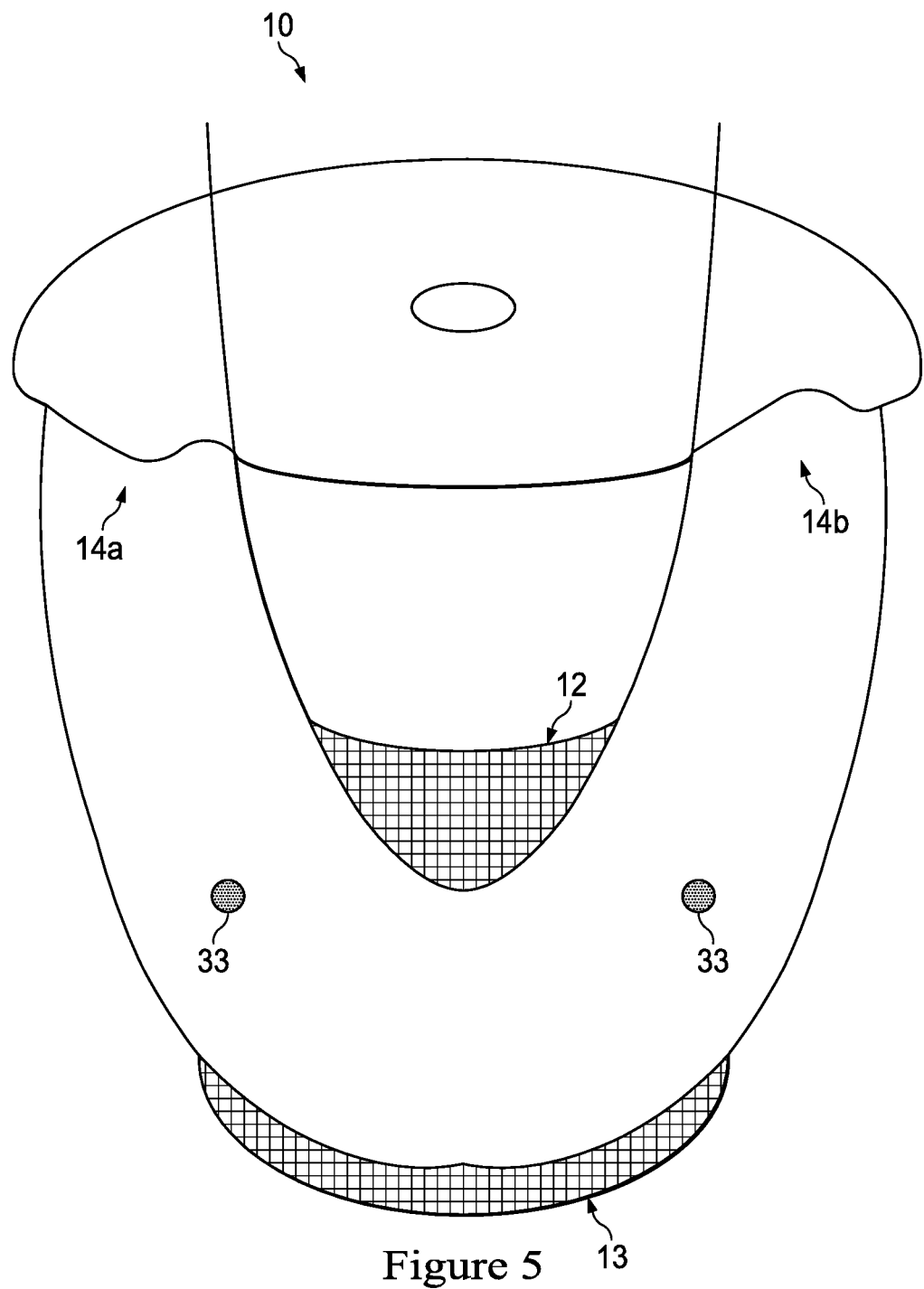
FIG. 5 is cutaway view from the side of pull-up when folded to an engaged position according to an embodiment.

FIG. 5 is cutaway view from the side of pull-up 10 when folded to an engaged position according to an embodiment. The pull-up 10 is shown having the first outer section 14a folded up in a first position (typically near an abdominal region of a human) and the second outer section 14b folded up in a second position (typically near a lower back region of a human). In this embodiment, the midsection 12 is shown on an inner patch portion of the pull-up 10 such that the inner midsection 12 contacts the skin of the wearer. Further, this embodiment also shows an outer midsection 13 that is similar to the inner midsection 12. That is, both the inner midsection 12 (sometimes called primary anti-microbial patch layer) and the outer midsection 13 (sometimes called secondary microbial patch layer) include embedded anti-microbial $Cu^+$, $Cu^{+++}$ ions to kill or reduce bacterial and viral infections. The outer midsection 13 provides additional contact with the inner thighs of the wearer and assists with handling excretion that may escape the pull-up 10. The embodiment of FIG. 4 shows two load and liquid micro-nano-copper-sensors 33.

Figure 6:
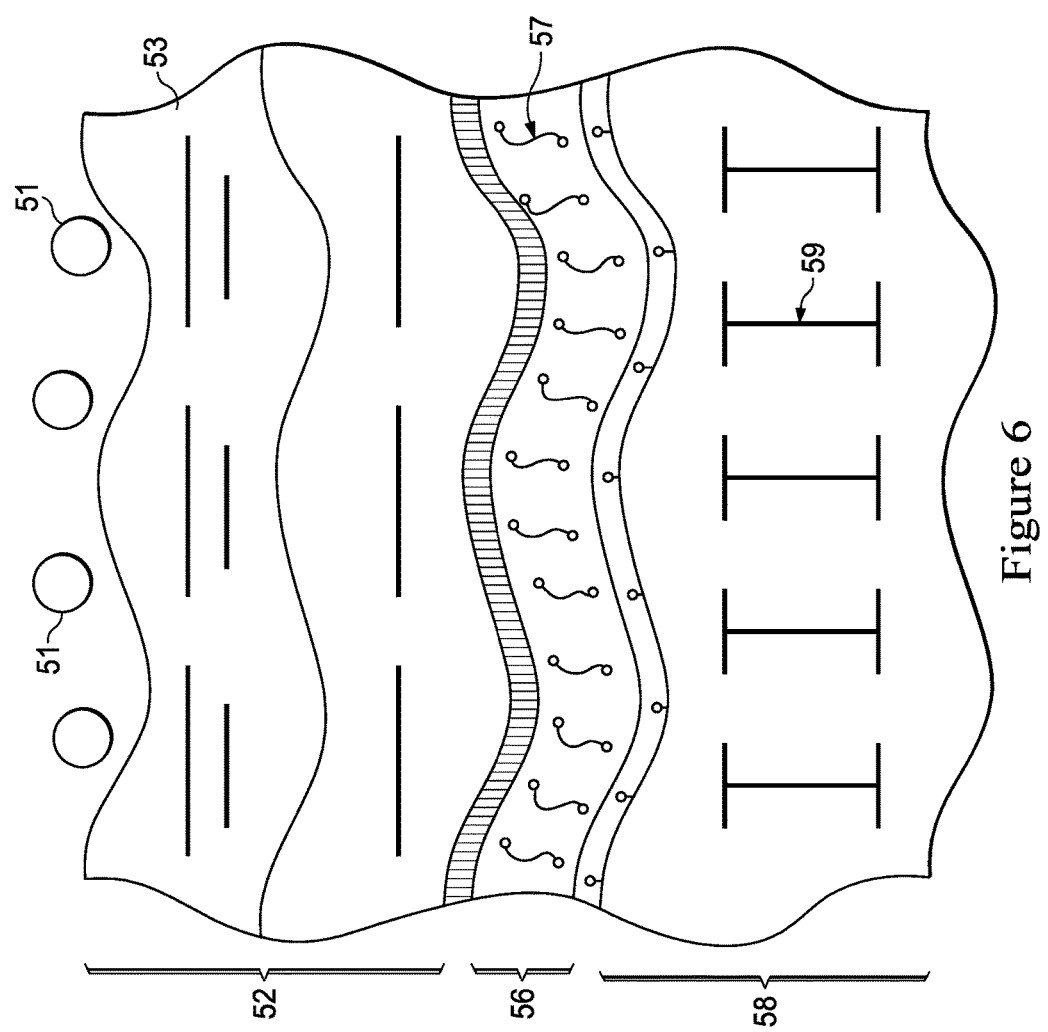
FIG. 6 is cutaway schematic view of a section of human skin anatomy showing various epidermal, dermal and sub-dermal layers so as to discuss the biological and chemical potential aspects of the pull-up 10 of FIG. 1.

FIG. 6 is cutaway view of a section of human skin anatomy showing various skin layers so as to discuss the biological and bio-chemical aspects of the smart pull-up 10 of FIG. 1. The anatomical regions at the skin or near the skin include an epidermis layer 52, a dermis layer 56 and a hypodermis layer 58. At or near the surface of the epidermis layer, there are sweat glands 51 that will excrete moisture to cool the skin. When excrement comes into contact with the human skin, moisture from the sweat glands and oxygen that is ambient may cause chemical reactions in the excrement that foster an environment whereby bacteria and viruses may grow and thrive. Such bacteria and viruses may interact with the epidermis layer 52 and cause infections, sores and other maladies of the skin.

As bacteria and microbes are allowed to remain and grow, the maladies may penetrate through the basal lamina 53 of the epidermis layer and through to the dermis layer 56 such that blood capillaries 57 are affected. In turn, the bacteria may further penetrate to the hypodermis layer 58 such that adipose fat tissue 59 is also affected by the malady. It is theorized that $Cu^+/Cu^{+++}$ ions can penetrate all the way to the adipose fat tissue 59 such that the bio-chemical process and biological process of bacteria growth can be interrupted or deterred. That is, the $Cu^+/Cu^{+++}$ ions may be suited to kill or reduce the bacteria or virus all the way into the skin as deep as 0.004 inches (e.g., at least as far as the adipose fat tissue 59 in the hypodermal layer 58.

Figure 7:
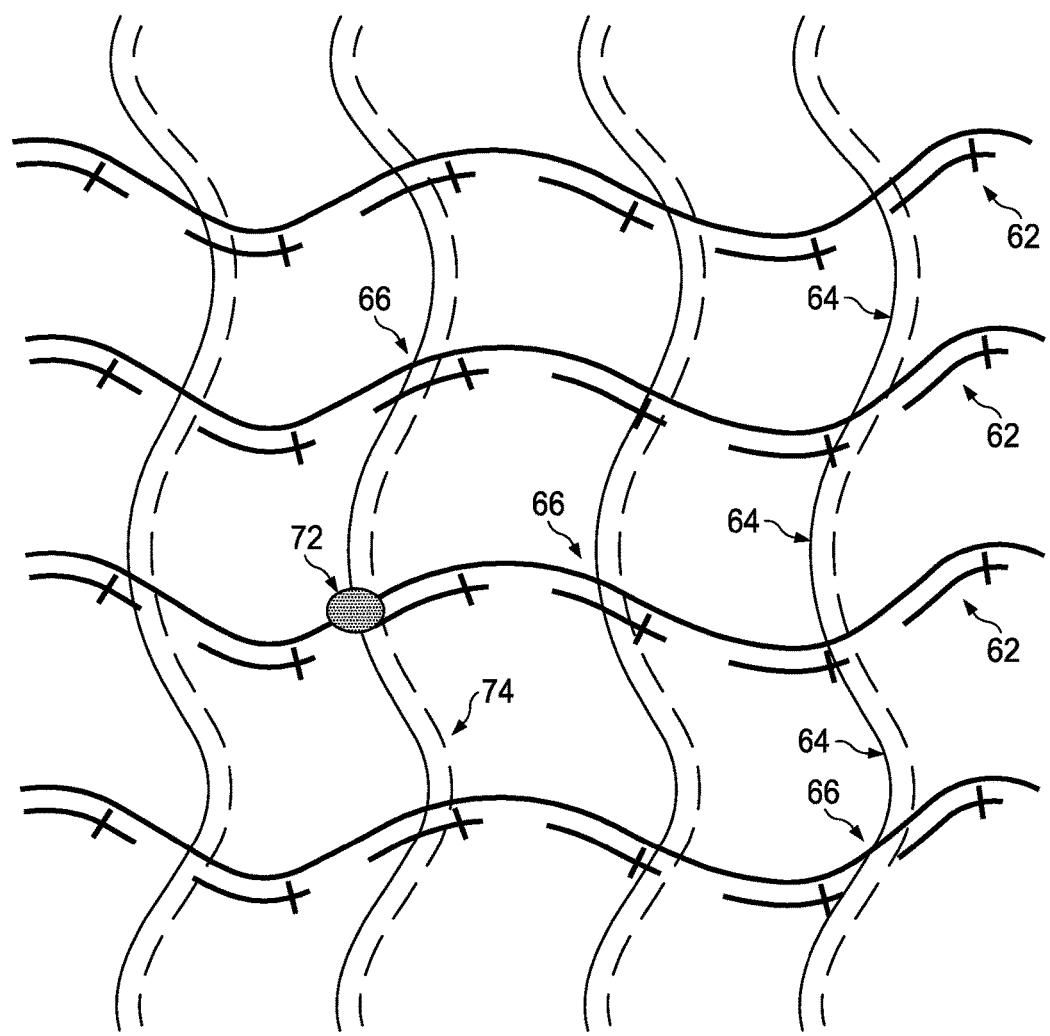
FIG. 7 is a magnified view of the center portion of the big tow design for natural fabric or paper form design layer of FIG. 1, according to an embodiment.

FIG. 7 is a magnified view of an antimicrobial material 60, which forms the center sublayer of layer 30 of FIG. 1, according to an embodiment. The material 60 includes balanced warp big tows 62 and fill big tows 64, which are made from fabric, natural-balanced tows (i.e., bundles of untwisted filaments) woven in a balanced, plain-weave pattern. The numbers of warp tows 62 and fill tows 64 per unit measurement (e.g., per inch) are equal such that there are the same number of warp tows per unit measurement as there are fill tows per the same unit measurement (this is a balanced weave). For example, the spacing between consecutive warp tows 62 and the spacing between consecutive fill tows 64 may be the same, and be no greater than 1/16" or finer.

Furthermore, the warp tows 62 and fill tows 64 can be made from the same natural fabric or superior material (e.g., paper) and have the same cross-sectional dimensions (e.g., diameter), or they can be made from different materials, and have different cross-sectional dimensions. For example, the fabric from which the warp tows 62 and fill tows 64 are made may be any suitable fabric that is one or more of the following: natural, super-absorbent, non-allergenic, and bio-degradable. Moreover, each warp tow 62 and each fill tow 64 may have a diameter in the range of approximately 0.015-

0.020 (big tow) or 0.00015 to 0.0020 (thin tow) inches. In addition, the warp tows 62 and fill tows 64 may have cross-sections with shapes other than a round microstructural-tow shape, such as flat cross-sections (see, e.g., http://www.easycomposites.co.uk/products/carbon-fibre-cloth-fabric/carbon-fibre-spread-tow-15mm-large-pattern-22-Twill.aspx, which is incorporated by reference).

The above-described weave structure and configuration of the material 60 provides balanced tension and compression in response to an abuse load to mitigate the stresses and strains caused by such a load or strain. That is, the weave structure and configuration of the material 60 allows the first and second layers 30 and 34 of the midsection 12 to distribute the abuse load or strain relatively uniformly so that the pull-up 10 feels more comfortable to the wearer and is less likely to rip or tear. For example, such an abuse load may be caused by movements of the wearer, or by solid excrement that is lodged between the wearer and the pull-up 10.

Furthermore, the above-described weave structure and configuration of the material 60 allows excrement to pass into and through the first layer 30 of the midsection 12 and into the air gap 32, but impedes excrement from leaking out of the air gap and back through the first layer to the wearer's skin. Each warp tow 62 and fill tow 64 includes at least one micro-copper filament 66, which provides the pull-up 10 (FIG. 1) with the antimicrobial properties described above. For example, each warp tow 62 and fill tow 64 may include one to three copper filaments 66, which have at least $Cu^+$ ions; the micro-copper filaments may also include $Cu^{+++}$ ions, and may even include $Cu^{++}$ ions. Although pure, uncoated micro $Cu^+$ filaments typically provide migration and diffusion of $Cu^+$ ions into human skin, through the action of ion electric potential, at a faster rate than $Cu^{++}$ or $Cu^{+++}$ filaments, other metals with complex ions may be used for the filaments. For example, the filaments 66 are made from a type of copper that includes $Cu^+$ ions and $Cu^{+++}$ ions because such raw-copper complex ions have a more active-state potential that may increase their antimicrobial efficacy and, therefore, may increase the antimicrobial rate or efficiency of the pull-up 10. Furthermore, these raw-copper complex ions may also increase the pull-up's efficacy in sanitizing excrement and other substances in the air gap 32. Moreover, each micro-copper filament 66, whatever its composition, may have a cross section on the order of 0.00004 to 0.006", which is smaller than the diameter of single strand of human hair.

By including micro-copper filaments 66 instead of, e.g., plated copper, the material 60 provides the antimicrobial properties of copper without residues or other byproducts that may be toxic to the wearer of the pull-up 10. Furthermore, the process used to manufacture the pull-up 10 may be less complex because no copper-adding plating step need be performed.

Still referring to FIG. 7, alternate embodiments of the material 60 are contemplated. For example, to save on micro-copper, the copper micro-filaments 66 may be included in only some of the warp tows 62 and fill tows 64, such as every two warp tows and every three fill tows, or vice-versa. Furthermore, the copper micro-filaments 66 may be in only one of the first layer 30 and second layer 34 instead of in both of these layers. Moreover, although described as forming at least a part of the first and second layers 30 and 34 of the midsection 12 (FIG. 1), the material 60 may also form at least a part the layer 40 of one or both of the outer sections 14a and 14b (FIG. 1).

In another embodiment, the material 60 may also include at least one nano-copper sensor 72 configured to sense excrement and to generate an indication of the sensed excrement. In more detail, the material 60 may have warp tows 62 or fill tows 64 that include filaments 74 of nano-copper sensor material instead of the standalone micro-copper filaments 66, and the combination of the nano-filaments 74 and copper filaments 66 form one or more nano-copper sensors 72. For example, the nanomaterial filaments 74 may be nanofibers. For purposes of example, the material 60 is described with the warp tows 62 including the micro-copper filaments 66 and the fill tows 64 including the nanomaterial fibers 74, it being understood that the description of the material 60 is similar with the warp tows including the nanomaterial fibers and the fill tows including the copper micro filaments. Further for purposes of example, the material 60 is described as including only one nano-copper sensor 72.

The micro-copper filaments 66 and nanomaterial fiber 74 form nodes of the nano-copper sensor 72 where the copper filaments cross over the nanomaterial fibers. It is noted, however, that at a node, the corresponding micro-copper filament is integrated with the corresponding nanomaterial fibers. As described below, the presence of liquid excrement, or the presence of a load caused by solid excrement, causes a reaction at the nodes that cause the nano-copper sensor 72 to change color at the nodes where an electro-chemical reaction oxidation is initiated; because the nodes are relatively close together, this color change spreads into non-nodal portions of the nano-copper sensor and thus resulting in the color difference.

In more detail, there exists an electric potential interaction between a copper ions/atoms 66 and a nano-fiber material filament 74 at a specific node. In the presence of a liquid, such as liquid from urine or loose feces, this electric potential causes, at a node 76 (shown in FIG. 8, which is an expansion of nano-copper sensor 72 shown in FIG. 7), ions from the corresponding nanomaterial tube 74 and ions (e.g., Cu+, Cu++, or Cu+++ ions) from the corresponding copper filament to migrate toward each other. Some of these ions may combine with one another to produce an ionic network that produce a color, such as red, which, therefore, indicates the presence of excrement in the material 60. Alternatively, the ions from the corresponding nanomaterial fiber 74, the ions from the corresponding copper filament 66, or both the nanomaterial tube ions and copper ions, may combine with one or more oxidative reactants in the liquid to produce a red color. Such ion migration and combination, and the resulting color generation, may also occur in response to a load/strain that reduces the distance between the copper filament 66 and the nano-fiber material 74 at the node, e.g., by straining the material 60 (this decrease in distance increases the electrical attraction between the nano-fiber material ions and copper ions, thus making them more prone to migration). Alternatively, the warp tow 62 containing the copper filament 66, the fill tow 64 containing the nanomaterial filament 74, or both of these warp and fill tows, may include a oxidative substance that reacts with the migrating copper ions or nanomaterial ions to produce another substance that has a color. In this latter example, the production of the other substance may also occur when the ion migration is induced by liquid. Therefore, the sensor 72 can be configured so that the color produced by liquid is different from the color produced by a load so that a caregiver can determine, by the color, whether the wearer most likely has most urinated, defecated, or both urinated and defecated.

Furthermore, the nano-copper sensor 72 can be configured to change color after excrement has been present for at least a threshold period of time. For example, the corresponding nanofilament 74 may include ions that migrate to the copper ions more slowly than other ions. So the first ions to interact with the copper ions produce a first color (e.g., green), and then at some time later, the slower ions interact with copper ions to product another color (e.g., red) to indicate that the excrement has been present, i.e., has persisted, for at least a threshold period of time (e.g., 30 minutes). Or the slower nanomaterial ions may interact with the already interacted faster nanomaterial ions and copper ions to form a second substance that has a different color from the first substance formed by the interaction of the faster nanomaterial ions and copper ions. Alternatively, the substance formed by the interaction of the migrating copper ions and nanomaterial ions may change naturally from a first color (e.g., green) to a second color (e.g., blue or red) over a predictable period of time (e.g., 30 minutes).

As described above, the material 60 may be configured to form multiple nano-copper sensors 72. For example, there may be breaks in either the copper filaments 66 or nanomaterial filaments 74, and these breaks define the boundaries between one nano-copper sensor 72 and another nano-copper sensor. Where the material has multiple nano-copper sensors 72, each nano-copper sensor may be configured to generate the same color(s) as the other nano-copper sensor, or to generate different color(s) relative to the other nano-copper sensors.

The following is a more detailed description of the structure and operation of the one or more nano-copper sensors 72 formed by the material 60, including the antimicrobial action of the copper ions provided by the copper filaments 66.

The one or more nano-copper sensors 72 may be formed from nanostructure/copper material that is formed by, e.g., 3D, 4D or 5D printing, at the various nodes of the fabric 60. In the presence of excrement or other excretions, the nanomaterial interacts with the copper ions to change color, where, as described above, the color may increase or decrease in intensity as time goes on to indicate a length of time that the excretion has been present. The nanomaterial in the filaments 74 can be designed to change from any first color (e.g., white or clear) to any second color (e.g., green, blue). The nanomaterials will change the micro structure of the copper ions to make color sensors. Embedding the copper into a conductive nano-tube takes the conductive electrical property of copper interspersed with conductive nanoparticles to form a very complex bio-inspired color sensor 72, which can indicate the presence of human excrement and other excretions. Moreover, such nano-copper sensors 72 can sense both a load and fluid. The novel integrated hybridized multi-walled conductive nanofiber/complex copper ions sensor (anti-microbial design technology) combines and integrates both the unique piezoelectric potential, ionic chemistry, and physical properties of both elements (nanomaterial and copper atoms). This integrated hybridized new sensor-antimicrobial design system acts both as a special type of autonomous or self-regulating sensor to detect both liquids and excrement-induced strains or load on the human skin, when wearing the smart wearable device pull-up undergarment 10 (FIG. 1) in any medical environment or home setting. This novel complex nanofiber sensor-copper ions antimicrobial integrated bio-inspired system design with nodal copper ions within the inverted spring shaped nanofiber microstructure sends the high electrical conductivity across the microstructure, which is picked up by the nodal complex copper ions. This now integrated complex nodal ions electrical signal picked up and beams this increased in electrical resistivity once in contact with bodily fluids, resulting in different colors due to the ionic oxidative conditions. The resulting different colors, as also may be shown on the sided flaperons of the smart wearable pull-up, in form of red for either bodily fluid or excrement, and thus could be seen by a caregiver to the wearer in any medical settings. On the other hand, the percentage of the same complex copper infused fibers within the fabric weave material is 0.0005%-15% of the membrane fail-safe patch area having secondary antimicrobial and antifungal effects by diffusing the ions biologically into the human skin at, for example, the gluteal region, and through this biological process the complex copper ions penetrate into any microbial membrane anatomy, and bind enzymes and integrate themselves into the microbes' DNA, thus depriving the microbes the ability to generate energy from the protein at the molecular-cellular level to regenerate and multiply and lead to infections at the lower extremities and gluteus. The additional biological benefits due to the redox reaction between the human epidermal, dermal, and the blood-tissue vessels could also lead to reduction in human skin oxidative stress that are normally cause by bacteria and fungi and other microbes within a medical environment. The sanitization of the human skin extremities and reduction of infection oxidative stress by the $Cu^+/Cu^{+++}$ copper ions would also lead to other additional biological positive effects such as improving the tissue oxygen circulation pathway at the point of potential infection, improving the health of surrounding tissues, epidermal, dermal, connective tissue, and creating a smart-sensor environment for other surrounding tissue from its integrated primary multi-functional system design, and also decreasing and sanitizing the odor causing infection environment. Biologically, the complex raw copper ions' diffusion into, e.g., the gluteal skin region, also creates a pathway for moisture adsorption within the local infection medical source environment, including soothing the local muscle by reduction of infection oxidative stress.

Still referring to FIG. 7, alternate embodiments of the material 60 are contemplated. For example, to save on copper, nanomaterial, or both, the copper filaments 66 and nanomaterial filaments 74 may be included in only some of the warp tows 62 and fill tows 64, respectively, such as every two warp tows and every three fill tows, or vice-versa. Furthermore, the copper filaments 66 and nanofilaments 74 may be included in only one of the layers 30 and 34 instead of in both of them, or only the nanofilaments 74 may be omitted from one of the layers 30 and 34 (such that this layer may lack a nano-copper sensor). Moreover, although described as forming the center sublayer of the layers 30 and 34 of the midsection 12 (FIG. 1), the material 60 may also form the layer 40 of one or both of the outer sections 14*a* and 14*b* of the pull-up 10 (FIG. 1).

Figure 8:
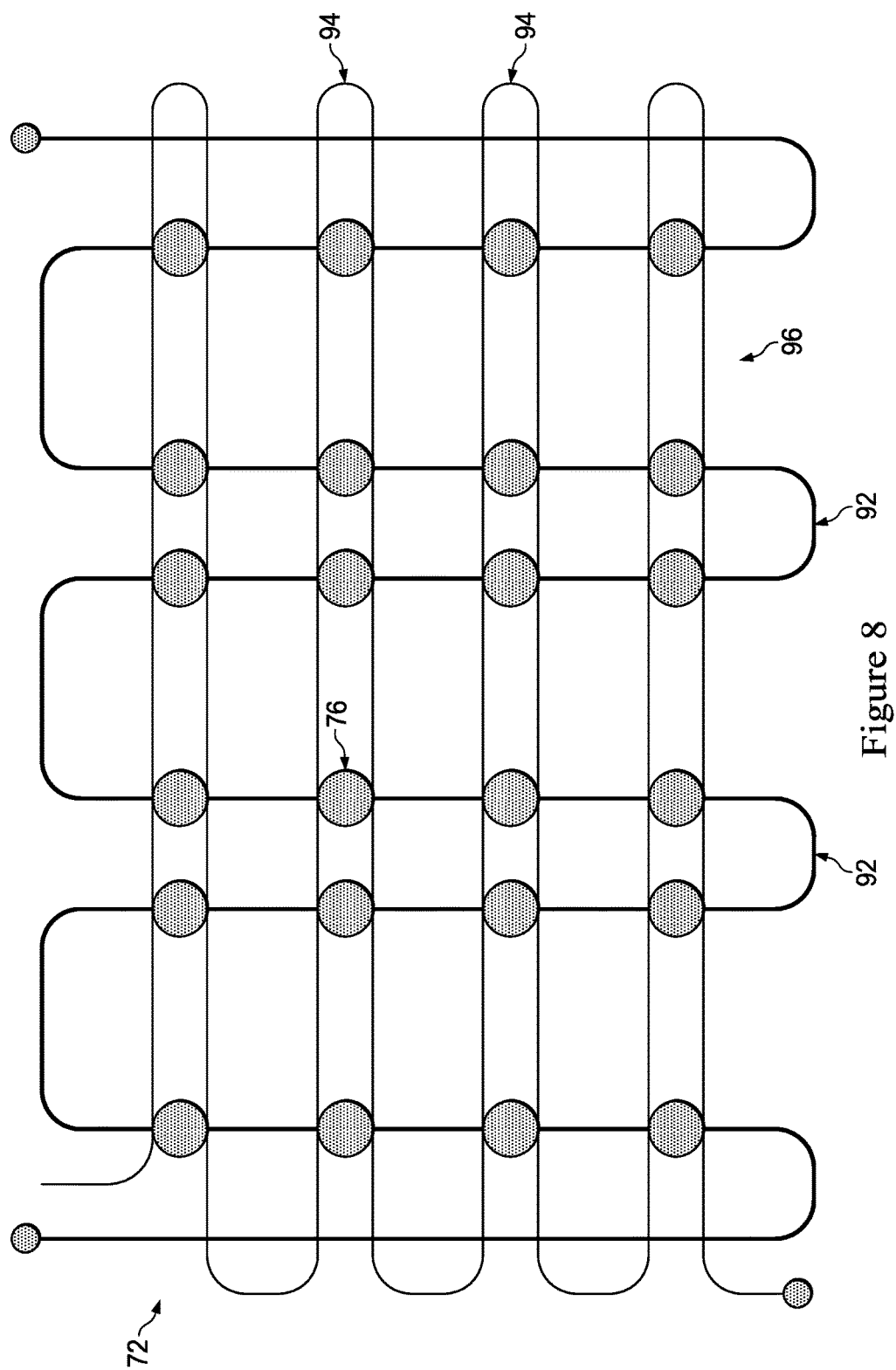
FIG. 8 is a plan view of a multi-functional nano-copper sensor that may be present in the material of the pull-up of FIG. 1 according to an embodiment.

FIG. 8 is a plan view of a nano-copper sensor 72 that may be present in the material 60 as discussed above with respect to FIG. 7 according to an embodiment. In some embodiments, the nano-copper sensor 72 can be a stand-alone sensor that does not form part the central sublayer of one or more of the first, second, and fourth layers 30, 34, and 40 of the pull-up 10 of FIG. 1. For example, one or more of the nanocopper sensors 72 can be attached (e.g., by stitching, gluing, or welding) to one or more of the layers 30, 34, and 40, or can be disposed in the air gap 32. Including the nanocopper sensor 72 in the pull-up 10 instead of embedding one or more nano-copper sensors 72 in one or more of the layers 30, 34, and 40 may reduce manufacturing complexity and cost for the pull-up, and including a standalone nano-copper sensor 72 in addition to the one or more nano-copper sensors 72 woven in can increase the excrement-sensing and excrement-notification abilities of the pull-up 10.

The nano-copper sensor 72 includes copper filaments 92, which can be similar to the copper filaments 66 of FIG. 6, nanomaterial filaments 94, which can be similar to the nanomaterial filaments 74 of FIG. 6, and a substrate 96, which can be made from any suitable material such as the foam material from which the outer sublayers are formed, and can include the same ion-reactive substances, as the warp tows 62 and fill tows 64 of FIG. 6. Furthermore, the copper filaments 92 and nanomaterial filaments 94 form nodes 76 where they cross over one another. Because the copper filaments 92 and nanomaterial filaments 94 form continuous electrical paths (as shown by the connected, looping ends of these features), small electrical currents will create ions at the nodes 76. The layout and materials are suited to produce $Cu^+/Cu^{+++}$ ions that are well suited for combating bacteria and viruses as discussed above.

Still referring to FIG. 8, alternate embodiments of the nano-copper sensor 72 are contemplated. For example, instead of the copper filaments 92 being disposed under the nanomaterial filaments 94, the copper filaments may be interwoven with the nanomaterial filaments, and the substrate 96 can be configured to prevent the copper filaments from contacting the nanomaterial filaments. Furthermore, the nano-copper sensor 72 can have any suitable shape, such as square, circular, rectangular, or triangular.

Figure 9:
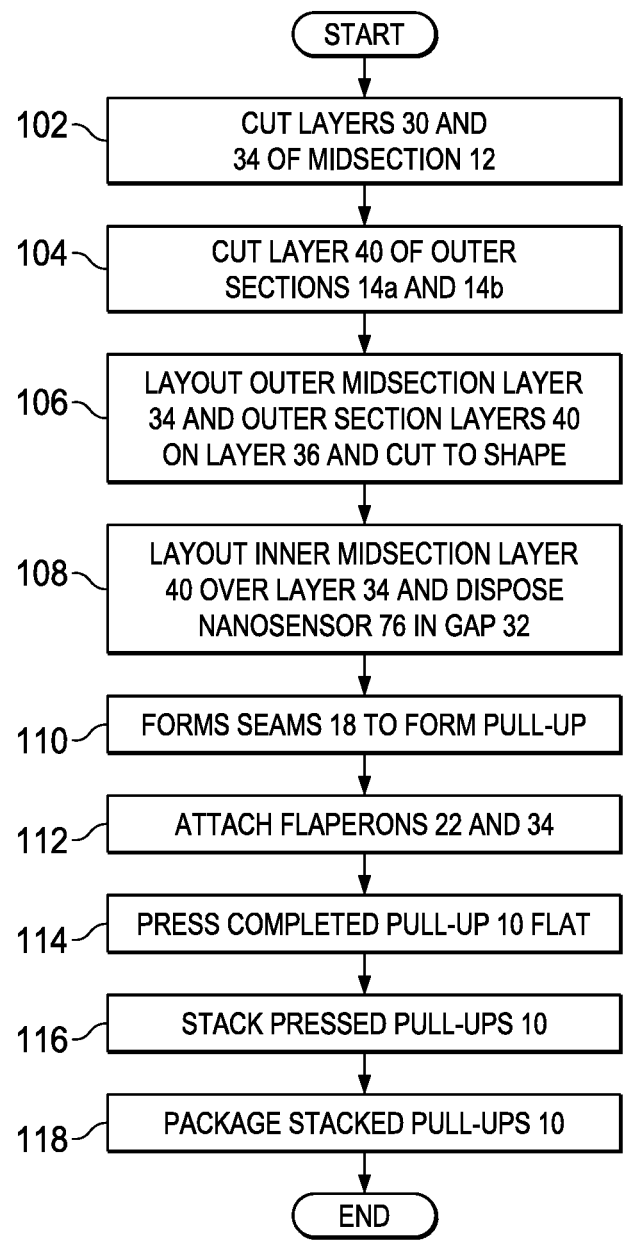
FIG. 9 is a flow chart of a process for manufacturing the pull-up of FIG. 1, according to an embodiment.

FIG. 9 is a flow diagram 100 of a process for forming the pull-up 10 of FIG. 1, according to an embodiment. At a step 102, the first and second layers 30 and 34 of the midsection 12 are cut from sheets that include either the material 60 of FIG. 8 as the center sublayer (both layers 30 and 34 may be cut from the same sheet).

Next, at a step 104, the layers 40 of the outer sections 14a and 14b of the pull-up 10 are cut from a sheet that includes the material 60 of FIG. 6 as the center sublayer. Then, at a step 106, the cut-out second and fourth layers 34 and 40 are laid out, in their to-be-assembled form, on a sheet of material from which the third layer 36 is to be formed, and the third layer 36 is cut to its final shape. If the third layer 36 is to be attached to the second and fourth layers 34 and 40 by an adhesive, then this adhesive is applied to the sheet of material before the cut-out layers 34 and 40 are laid out on the sheet.

Next, at a step 108, the cut-out first layer 30 is positioned over the second layer 34. If one or more nano-copper sensors 72 are to be disposed in the gap 32, then these one or more nano-copper sensors are positioned on the second layer 34 before the first layer 30 is positioned over the second layer 34.

Then, at a step 110, the seams 18a and 18b are formed (e.g., by "welding," by gluing, or by stitching) to secure the outer sections 14a and 14b to the respective ends 16a and 16b of the midsection 12 and to form the air gap 32. Next, if the flaperons 22 and 24 are not integral with the layers 40 of the outer sections 14a and 14b, then at a step 112, the flaperons are attached to the outer sections by, e.g., "welding," gluing, or stitching or other manufacturing techniques. Then at a step 114, the completed pull-up 10 is pressed flat in its open position (the position shown in FIG. 1), and at a step 116, the pressed pull-up is stacked with other completed pull-ups in preparation for packaging the pull-ups. Next, at a step 118, the stacked pull-ups 10 are packaged for distribution.

Alternate embodiments of the manufacturing process are contemplated. For example, some manufacturing steps may have been omitted from FIG. 9, and one or more of the steps detailed in FIG. 9 may be omitted. Furthermore, the steps 102-118 may be performed in an order that is different from the order described above.

Figure 10:
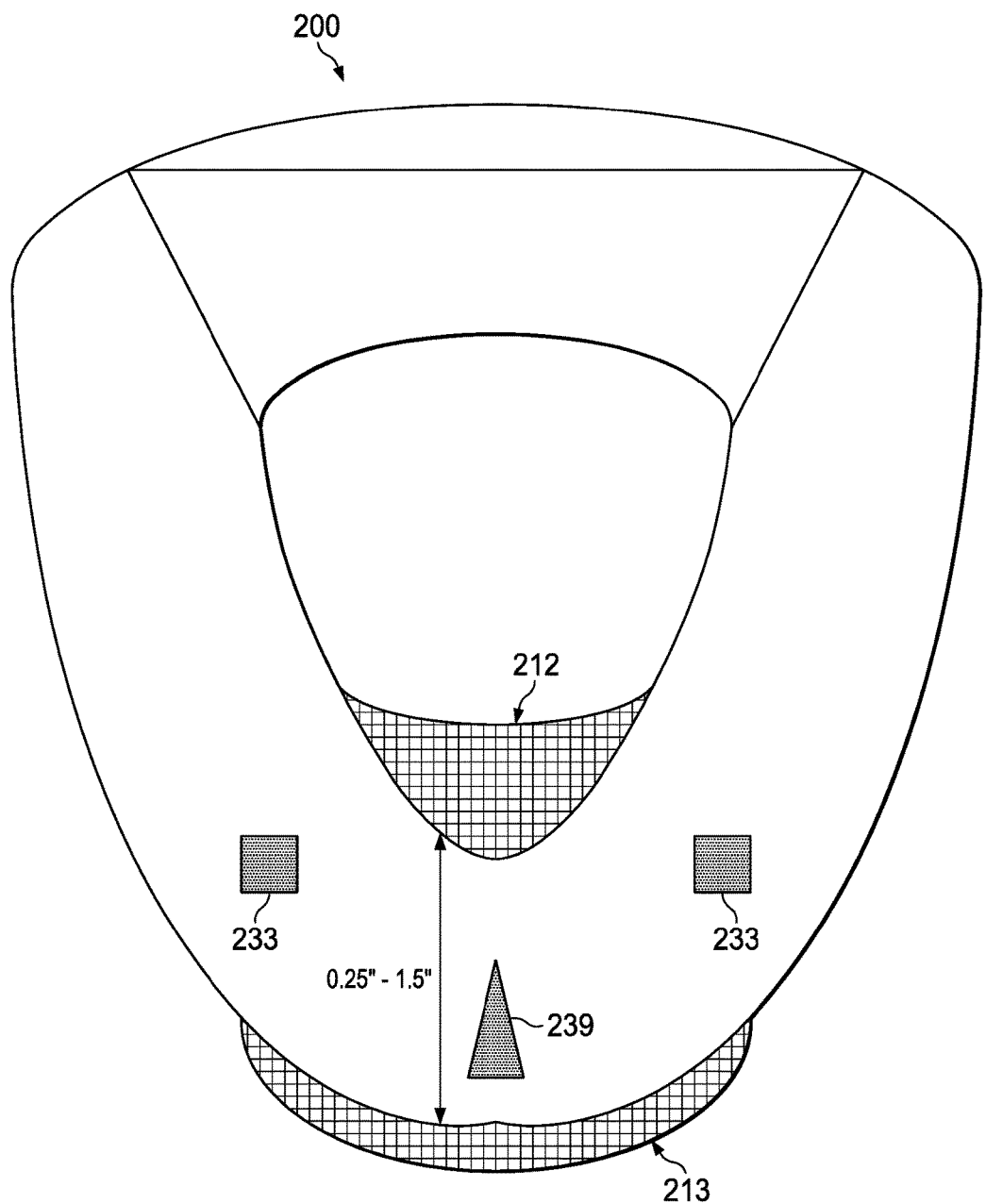
FIG. 10 is a side view of an alternative embodiment of a pull-up shown in an engaged form according to an embodiment.

FIG. 10 is a side view of an alternative embodiment of a pull-up shown in an engaged form according to an embodiment. The pull-up 200 is shown with a straight side with a scaffolded elastic waist that may be parallel on either side and without attachment flaperons. This embodiment may be ideal for healthy adults for comfort and convenience. In this embodiment, the midsection 212 is shown on an inner membrane patch portion of the pull-up 200 such that the inner midsection 212 contacts the skin of the wearer. Further, this embodiment also shows an outer midsection 13 that is similar to the inner midsection 212. That is, both the inner midsection 212 (sometimes called primary anti-microbial layer) and the outer midsection 213 (sometimes called secondary microbial patch layer) include embedded antimicrobial Cu+, Cu+++ microfilaments to kill/reduce bacterial and viral infections. The outer midsection 213 provides additional contact with the inner thighs of the wearer and assists with handling excretion that may escape the pull-up 200. Further yet, the distance between the inner midsection 212 and the outer midsection 213 may be typically 0.25 inches to 1.5 inches thereby providing a percolating gap 239 reserve membrane to isolate bacteria from oxygen so as to disrupt or delay the biochemical process.

The embodiment of FIG. 10 shows two load and liquid micro-nano-copper-sensors 233. These micro nano-copper sensors are self-regulated to detect the presence of liquid excretion or solid excretion. In various embodiments, more than two may be used and various micro-nano-copper-sensors 233 may be configured to detect only liquid excretion or only solid excretion. Further, the nano-sensors 233 may track elapsed time since first detection such that the data and information about parameters being sensed may be transferred to a local mobile device, if so desired within a medical settings or wearer.

From the foregoing it will be appreciated that, although specific embodiments have been described herein for purposes of illustration, various modifications may be made without deviating from the spirit and scope of the disclosure. Furthermore, where an alternative is disclosed for a particular embodiment, this alternative may also apply to other embodiments even if not specifically stated. Furthermore, one or more components of a described apparatus or system may have been omitted from the description for clarity or another reason. Moreover, one or more components of a described apparatus or system that have been included in the description may be omitted from the apparatus or system.

What is claimed is:

1. A manufacture that comprises:
   at least one outer section;
   a midsection attached to the at least one outer section such that the midsection comprises:
   a first antimicrobial layer configured to contact a wearer's body, such that the first antimicrobial layer comprises a center sublayer between two outer sublayers, such that each outer sublayer comprises a respective core that comprises a micro foam, and the center sublayer comprises:

a balance plain weave pattern such that a plurality of first warp tows in the first antimicrobial layer each respectively comprise a first 1 to 3 filaments such that a spacing between adjacent first warp tows in the plurality of first warp tows remains within 1/16 of an inch, and each filament in the first 1 to 3 filaments respectively consists of a cross section on an order of 0.00004 to 0.006 inches and a first copper that comprises a at least one of first Cu+ ions or first Cu+++ ions; and a plurality of first fill tows such that a spacing between adjacent first fill tows in the plurality of first fill tows remains within 1/16 of an inch, and each fill tow in the plurality of first fill tows respectively comprises a first nanomaterial that consists of a second copper that comprises 0.0005 to 15% of material that comprises the first fill tows and at least one of second Cu+ ions or second Cu+++ ions, such that each first warp tow and each first fill tow comprise a width in a range of approximately at least one of: 0.015 to 0.020 inches, or 0.00015 to 0.0020 inches; and a second antimicrobial layer disposed adjacent to the first antimicrobial layer, such that the second antimicrobial layer comprises:

a balance plain weave pattern such that a plurality of second warp tows in the second antimicrobial layer comprise a spacing between adjacent second warp tows in the plurality of second warp tows that remains within 1/16 of an inch, and each second warp tow in the plurality of second warp tows respectively comprises a second 1 to 3 filaments such that each filament in the second 1 to 3 elements respectively consists of a cross section on an order of 0.00004 to 0.006 inches and a third copper that comprises at least one of third Cu+ ions or third Cu+++ ions; and a plurality of second fill tows such that a spacing between adjacent second fill tows in the plurality of second fill tows remains within 1/16 of an inch, and such that each second fill tow in the plurality of second fill tows respectively comprises a second nanomaterial that consists of a fourth copper that comprises at least one of fourth Cu+ ions or fourth Cu+++ ions, such that each second warp tow and each second fill tow comprise a width in a range of approximately at least one of: 0.015 to 0.020 inches, or 0.00015 to 0.0020 inches; and a gap disposed between the first and the second antimicrobial layers, such that the gap consists of air.

2. The manufacture of claim 1, further comprising:
the micro foam comprising a cellulose configured to absorb and hold a liquid; and
the at least one outer section comprises a third layer that comprises a balance of third warp tows and third fill tows in a plain-weave pattern.

3. The manufacture of claim 1, wherein the outer section comprises:
a third layer that comprises a balance of third warp tows and third fill tows in a plain-weave pattern; and
a third 1 to 3 filaments respectively disposed in a plurality of third warp tows, such that each of the second 1 to 3 filaments consist of a third copper that comprises at least one of a third Cu+ ions or a third Cu+++ ions.

4. The manufacture of claim 1, wherein the outer section comprises adhesive flaperons.

5. The manufacture of claim 1, further comprising the first and the second antimicrobial layers each configured to absorb moisture.

6. The manufacture of claim 1, wherein each of the first and the second antimicrobial layers comprise:
nanomaterial that consists of copper, such that the nanomaterial and the second 1 to 3 filaments, form at least one nano-copper sensor configured to detect excrement.

7. The manufacture of claim 1, wherein at least one of the first and the second antimicrobial layers comprises a respective sublayer of foam-like substance disposed over at least one side of the first or second warp tows or the first or second fill tows.

8. The manufacture of claim 1, wherein each of the first and of the second 1 to 3 filaments comprises Cu+++ ions configured to kill bacteria and virus located down to 0.004 inches below a surface of a skin.

9. The manufacture of claim 1, further comprising the gap configured to hold excrement propagated through the first antimicrobial layer of the midsection.

10. The manufacture of claim 1, further comprising a third layer disposed adjacent to a side of the second antimicrobial layer opposite to the gap and configured to impede an excrement leak from the second antimicrobial layer.

11. The manufacture of claim 1, further comprising:
a first nano-copper sensor disposed adjacent to the first antimicrobial layer and configured to detect excrement; and
a second nano-copper sensor disposed adjacent the second antimicrobial layer and configured to detect excrement.

12. The manufacture of claim 11, wherein the first and the second nano-copper sensor each comprises respectively:
nanomaterial and each filament configured such that a space exists between the nanomaterial and the filament.

13. The manufacture of claim 11, wherein the first and the second nano-copper sensor each comprise respectively:
a warp tow that comprises one of a nanomaterial and a micro filament of a copper that comprises at least Cu+ ions; and
a fill tow that comprises the other of the nanomaterial and the micro filament and configured such that a space exists between the nanomaterial and the micro filament.

14. The manufacture of claim 11, wherein the first and the second nano-copper sensor are disposed in the first and the second antimicrobial layers, respectively.

15. The manufacture of claim 11, further comprising a third nano-copper sensor disposed on the second antimicrobial layer.

16. A nano-copper sensor configured to sense at least one of: a load, a strain, or a liquid, via a configuration that comprises:
rows of nanofibers spaced apart from one another, such that the nanofibers consist of copper; and
filaments spaced apart from each other and from the rows of nanofibers, and disposed substantially perpendicular to the rows of nanofibers, such that each filament in the filaments consists of a continuous filament that consists of a cross section on an order of 0.00004 to 0.006 inches and a copper that comprises at least one of: Cu+ ions or Cu+++ ions.

17. The nano-copper sensor-of claim 16, further comprising the rows of nanofibers and the filaments being interwoven.

18. The nano-copper sensor-of claim 16, further comprising:
   warp tows that comprise the filaments; and
   fill tows that comprise the rows of nanofibers.

19. The nano-copper sensor of claim 16, further comprising:
   a substrate that comprises sides, wherein the rows of nanofibers are disposed on one side of the substrate, and wherein the filaments are disposed on another side of the substrate.

20. The nano-copper sensor-of claim 16, wherein the filaments comprise the Cu+ ions configured to kill bacteria and virus located down to 0.004 inches below a surface of a skin.

21. The nano-copper sensor-of claim 16, wherein the filaments comprise the Cu+ and the Cu+++ ions configured to kill bacteria and virus located down to 0.004 inches below a surface of a skin.

22. A process for indicating excrement, the process comprising:
   sensing excrement via sensing at least one of: a load, a strain, or a liquid, via a nano-copper sensor comprising rows of nanofibers spaced apart from one another, and copper filaments spaced apart from the rows of nanofibers and from one another and disposed substantially perpendicular to the rows of the nanofibers, the nanofibers consisting of copper, and each filament in the filaments consisting of a continuous filament consisting of a cross section on an order of 0.00004 to 0.006 inches and a copper comprising at least one of: second Cu+ ions or second Cu+++ ions; and
   generating, in response to sensing the excrement, an excrement indication via the nano-copper sensor.

23. The process of claim 22, further comprising generating the excrement indication via causing the nano-copper sensor to change color.

24. The process of claim 22, further comprising generating, in response to sensing the excrement for longer than a threshold period of time, an excrement-persistence indication via the nano-copper sensor.

25. The process of claim 22, further comprising:
   causing the nano-copper sensor to change to a first color; and
   causing the nano-copper sensor to change from the first color to a second color in response to the nano-copper sensor-sensing the excrement for longer than a threshold period of time.

26. A process of forming a wearable weave, the process comprising:
   attaching a first outer section of a wearable weave to a first end of a midsection of the wearable weave, the midsection comprising:
      a first antimicrobial layer configured to contact a wearer's body, the first antimicrobial layer comprising a center sublayer between two outer sublayers, each outer sublayer comprising a respective core comprising a micro foam, the center sublayer comprising:
         a balance plain weave pattern such that a spacing between adjacent first warp tows in a plurality of first warp tows remains within 1/16 of an inch, and such that the plurality of first warp tows in the first antimicrobial layer each respectively comprise a first 1 to 3 filaments, each filament in the first 1 to 3 elements respectively consisting of a cross section on an order of 0.00004 to 0.006 inches, and a first copper comprising at least one of first Cu+ ions or first Cu+++ ions; and
         a plurality of first fill tows such that a spacing between adjacent first fill tows in the plurality of first fill tows remains within 1/16 of an inch, and such that each first fill tow in the plurality of first fill tows respectively comprises a first nanomaterial consisting of a second copper comprising 0.0005 to 15% of material comprising the first fill tows and at least one of second Cu+ ions or second Cu+++ ions, each first warp tow and each first fill tow comprising a width in a range of approximately at least one of: 0.015 to 0.020 inches or 0.00015 to 0.0020 inches;
      a second antimicrobial layer disposed adjacent to the first antimicrobial layer, the second antimicrobial layer comprising:
         a balance plain weave pattern such that a plurality of second warp tows in the second antimicrobial layer comprise a spacing between adjacent second warp tows in the plurality of second warp tows that remains within 1/16 of an inch, and each second warp tow in the plurality of second warp tows each respectively comprise a second 1 to 3 filaments, such that each filament in the second 1 to 3 elements respectively consists of a cross section on an order of 0.00004 to 0.006 inches and a third copper comprising at least one of third Cu+ ions or third Cu+++ ions; and
         a plurality of second fill tows such that a spacing between adjacent second fill tows in the plurality of second fill tows remains within 1/16 of an inch, and such that each second fill tow in the plurality of second fill tows comprises a second nanomaterial consisting of a fourth copper comprising at least one of fourth Cu+ ions or fourth Cu+++ ions, each second warp tow and each second fill tow comprising a width in a range of approximately at least one of: 0.015 to 0.020 inches or 0.00015 to 0.0020 inches; and
      a gap disposed between the first and the second antimicrobial layers such that the gap consists of air; and
   attaching a second outer section of the wearable weave to a second end of the midsection of the wearable weave.

27. The process of claim 26, further comprising:
   the micro foam comprising a cellulose for absorbing and holding a liquid;
   stitching the first outer section to the first end of the midsection; and
   stitching the second outer section to the second end of the midsection.

28. The process of claim 26, further comprising:
   adhering the first outer section to the first end of the midsection; and
   adhering the second outer section to the second end of the midsection.

* * * * *